(12) United States Patent
Baxi et al.

(10) Patent No.: US 9,724,003 B2
(45) Date of Patent: Aug. 8, 2017

(54) ULTRA-LOW POWER CONTINUOUS HEART RATE SENSING IN WEARABLE DEVICES

(71) Applicant: Intel Corporation, Santa Clara, CA (US)

(72) Inventors: Amit S. Baxi, Thane (IN); Vincent S. Mageshkumar, Navi Mumbai (IN)

(73) Assignee: Intel Corporation, Santa Clara, CA (US)

(*) Notice: Subject to any disclaimer, the term of this patent is extended or adjusted under 35 U.S.C. 154(b) by 124 days.

(21) Appl. No.: 14/541,275

(22) Filed: Nov. 14, 2014

(65) Prior Publication Data

US 2016/0135698 A1    May 19, 2016

(51) Int. Cl.
    A61B 5/02     (2006.01)
    A61B 5/024    (2006.01)
    A61B 5/00     (2006.01)
    A61B 5/11     (2006.01)

(52) U.S. Cl.
    CPC ...... *A61B 5/02438* (2013.01); *A61B 5/02416* (2013.01); *A61B 5/1118* (2013.01); *A61B 5/681* (2013.01); *A61B 5/7225* (2013.01); *A61B 5/7285* (2013.01); *A61B 2560/0209* (2013.01); *A61B 2562/0219* (2013.01)

(58) Field of Classification Search
    CPC .... A61B 2560/0209; A61B 2562/0219; A61B 5/02416; A61B 5/02438; A61B 5/1118; A61B 5/681; A61B 5/7225; A61B 5/7285
    See application file for complete search history.

(56) References Cited

U.S. PATENT DOCUMENTS

| 2004/0138568 | A1  | 7/2004  | Lo et al. |
| 2010/0049010 | A1  | 2/2010  | Goldreich |
| 2014/0249430 | A1  | 9/2014  | Sims et al. |
| 2014/0288435 | A1* | 9/2014  | Richards ............ A61B 5/02427 600/479 |
| 2014/0297218 | A1  | 10/2014 | Yuen |

(Continued)

FOREIGN PATENT DOCUMENTS

| CN | 104055499 A | 9/2014 |
| TW | 201112179 A | 4/2011 |
| TW | I455060 B   | 10/2014 |

(Continued)

OTHER PUBLICATIONS

International Search Report and Written Opinion for PCT Application PCT/US2015/058850, mailed on Feb. 29, 2016, 13 pages.

(Continued)

*Primary Examiner* — Mark Remaly
(74) *Attorney, Agent, or Firm* — Jordan IP Law, LLC

(57) ABSTRACT

Systems and methods may provide for a piezoelectric film that generates an excitation signal in response to pressure variations on a surface of the piezoelectric film and an analog front end coupled to the piezoelectric film, wherein the analog front end generates a first measurement signal based on the excitation signal. Additionally, a heart rate monitor may be coupled to the analog front end, wherein the heart rate monitor generates a heart rate measurement based on the first measurement signal. In one example, the analog front end includes a single stage amplifier.

18 Claims, 2 Drawing Sheets

(56) References Cited

U.S. PATENT DOCUMENTS

2014/0358012 A1* 12/2014 Richards ............ A61B 5/02438
600/479

FOREIGN PATENT DOCUMENTS

TW      I543746 B    8/2016
WO    0230277 A2   4/2002

OTHER PUBLICATIONS

Basis Science, Inc., Basis B1 Band Presents the Whole Picture—in Real Time, All the Time, Dec. 1, 2014, V.101411, 6 pages.
Sarah Hilmer, Mio's Latest Breakthrough Product, the Mio LINK Heart Rate Wristband, Is Now Available, Apr. 11, 2014, Vancouver, 2 pages.
Office Action for Taiwan Patent Application 104133045, dated May 31, 2017, 28 pages including 14 pages of English translation.

* cited by examiner

ULTRA-LOW POWER CONTINUOUS HEART RATE SENSING IN WEARABLE DEVICES

TECHNICAL FIELD

Embodiments generally relate to heart rate sensing. More particularly, embodiments relate to ultra-low power continuous heart rate sensing in wearable devices.

BACKGROUND

Wearable heart rate sensors may typically employ photoplethysmography (PPG) techniques in which one or more light emitting diodes (LEDs) illuminate the skin of the wearer and changes in light reflected from the skin are measured as a function of pulsatile blood flow. While such an approach may be suitable under certain circumstances, there remains considerable room for improvement. For example, driving the LEDs may involve a relatively large amount of power consumption, which may have a negative impact on battery life, particularly in wearable sensors. Moreover, the accuracy of the reflected light in measuring pulsatile blood flow may be dependent on skin color as well as muscle tissue perfusion.

BRIEF DESCRIPTION OF THE DRAWINGS

The various advantages of the embodiments will become apparent to one skilled in the art by reading the following specification and appended claims, and by referencing the following drawings, in which:

DESCRIPTION OF EMBODIMENTS

Figure 1A:
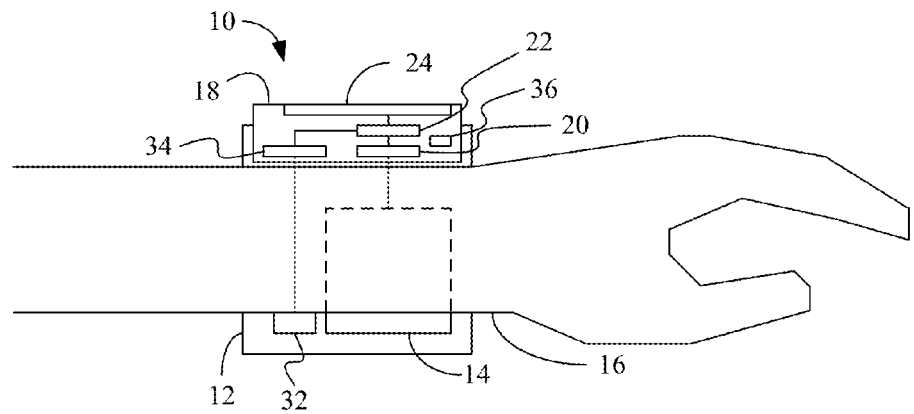
FIGS. 1A and 1B are a sectional side view and an end view, respectively, of an example of a wearable system according to an embodiment.
Figure 1B:
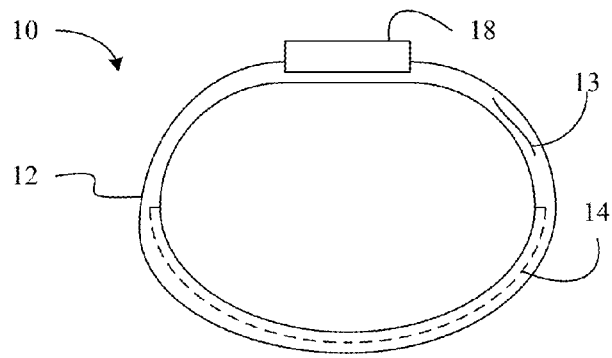

Turning now to FIGS. 1A and 1B, a wearable system 10 is shown. In the illustrated example, the wearable system 10 is worn on the wrist of an individual in order to take heart rate measurements. The wearable system 10 may alternatively be configured to be worn on other body parts such as, for example, the head, neck and other portions of the body in which pulsatile blood flow may be detected at the skin (e.g., near arterial sites in the subcutaneous tissue). In general, a wristband 12 of the wearable system 10 may include a piezoelectric film 14 (or an array of small piezoelectric elements) having one or more surfaces exposed to the interior region of the wearable system 10 so that the surface(s) of the piezoelectric film 14 come into contact with the skin 16 of the wrist either directly or through another layer of insulating film. The terms "piezoelectric film" and "array of small piezoelectric sensors" are used interchangeably herein. The piezoelectric film 14 may generate an excitation signal in response to pressure variations on the surface of the piezoelectric film 14 as a result of pulsatile blood flow beneath the skin 16 of the wearer. As will be discussed in greater detail, the piezoelectric film 14 may obviate concerns regarding power consumption, battery life, skin color, muscle tissue perfusion, and so forth.

An electrical housing 18 may be coupled to the wristband 12, wherein the illustrated electrical housing 18 includes an analog front end 20 coupled to the piezoelectric film 14. The analog front end 20 may generate a first measurement signal based on the excitation signal from the piezoelectric film 14. The illustrated electrical housing 18 also includes a heart rate monitor 22 coupled to the analog front end 20, wherein the heart rate monitor 22 may generate a heart rate measurement based on the first measurement signal. Additionally, a user interface 24 (e.g., display, speaker) coupled to the heart rate monitor 22 may output the heart rate measurement for external observation.

Of particular note is that the illustrated piezoelectric film 14 generates the excitation signal without any external power source such as, for example, a battery. As a result, the wearable system 10 may have relatively low power consumption. Indeed, the low power operability of the wearable system 10 may enable continuous heart rate measurements to be generated without concern over battery life. Moreover, because the illustrated piezoelectric film 14 does not rely on optical measurements, the heart rate measurements made by the wearable system 10 may not be dependent on skin color or muscle tissue perfusion.

Figure 2:
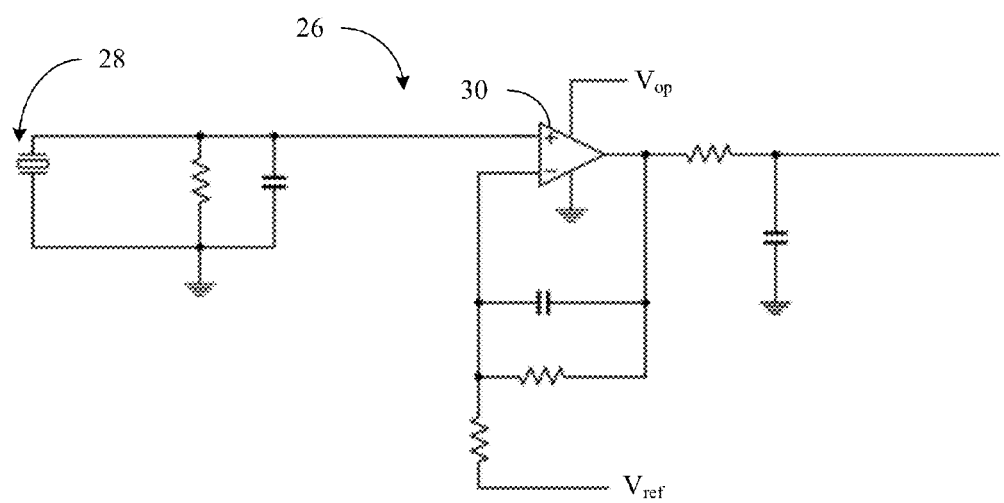
FIG. 2 is a schematic diagram of an example of an analog front end according to an embodiment.
Figure 3:
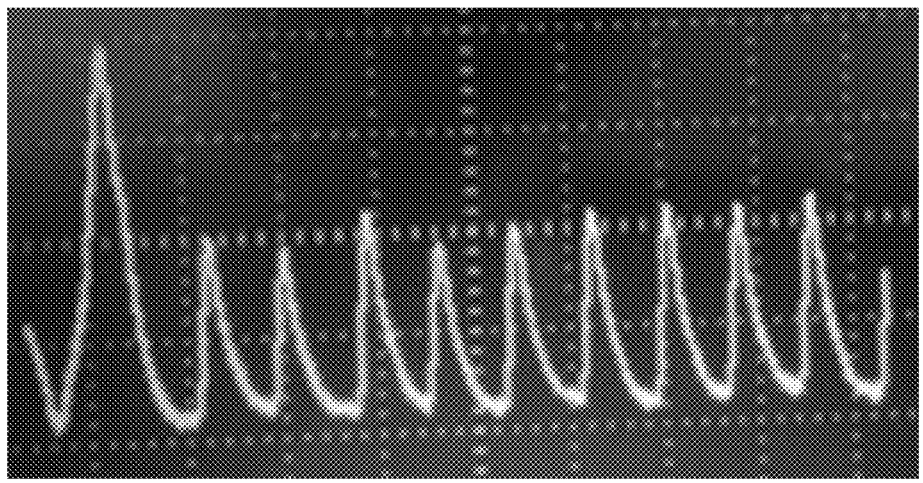
FIG. 3 is a plot of an example of a measurement signal according to an embodiment.

FIG. 2 shows one possible embodiment of an analog front end 26 to generate measurement signals. The analog front end 26 may be readily substituted for the analog front end 20 (FIG. 1A), already discussed. In the illustrated example, a piezoelectric film 28, which may be readily substituted for the piezoelectric film 14 (FIG. 1), generates an excitation signal that is a function of the pressure variations applied to the surface of the piezoelectric film 14 as a result of pulsatile blood flow. A signal amplifier 30 (e.g., operational amplifier) having an operational voltage ($V_{op}$) and a reference voltage ($V_{ref}$) may generate an analog measurement signal that is proportional to the voltage difference between the excitation signal and the reference voltage. In addition to the relatively low power requirements of the illustrated amplifier 30, fewer parts and less printed circuit board (PCB) space usage may be achieved via the illustrated approach. Although the illustrated amplifier 30 is a single-stage amplifier, the analog front end 26 may alternatively include multi-stage amplifiers as well. FIG. 3 shows an example of a measurement signal 31 generated by the analog front end 26.

Returning to FIGS. 1A and 1B, a hybrid piezoelectric/optical solution may be used to achieve greater accuracy. In this regard, if the wearer of the system 10 engages in intense levels of activity (e.g., heavy exercise versus sedentary/moderate activity), the piezoelectric film 14 may be susceptible to motion artifacts. Accordingly, the illustrated wearable system 10 also includes an optical module 32 (e.g., photoplethysmography/PPG module) coupled to the heart rate monitor 22 via an activity level monitor 34. The activity level monitor 34 may activate the optical module 32 in response to a physical activity condition being met (e.g., an activity threshold is exceeded).

The activity level monitor 34 may determine whether the physical activity condition is met based on the first measurement signal from the analog front end 20 and the piezoelectric film 14. Thus, if the first measurement signal exhibits voltage levels and/or swings that are greater than would be expected from pulsatile blood flow, the activity level monitor 34 might conclude that the physical activity condition is met. The activity level monitor 34 may also determine whether the physical activity condition is met based on another signal such as, for example, an accelerometer signal from an accelerometer 36 embedded in the wearable system 10.

Accordingly, the optical module 32 may generate a second measurement signal when the optical module 32 is activated, wherein the illustrated heart rate monitor 22 generates the heart rate measurement based on the second measurement signal when the second measurement signal is received from the optical module 32 via the activity level monitor 34. If, on the other hand, the physical activity condition is not met, the illustrated activity level monitor 34 deactivates the optical module 32 and the heart rate measurements are made based on the first measurement signal from the analog front end 20, as already discussed. Thus, the piezoelectric film 14 might be used to generate heart rate measurements during periods of sedentary to moderate activity (e.g., the majority of the time for most individuals).

The wristband 12 may be configured to ensure proper positioning of the piezoelectric film 14 relative to the arterial sites in the subcutaneous tissue as well as optimal pressure between the piezoelectric film 14 and the skin 16 in order to capture readings. For example, the piezoelectric film 14 may extend around a substantial circumference of the inner diameter of the wristband 12 so as to increase the likelihood of contact being made near the arteries. Additionally, the wristband 12 may include a stretch sensor 13 made, for example, from conductive elastomers and/or conductive fabric that enables the monitoring of stretch and tension of the wristband 12 and position. The monitored data may in turn be used to convey repositioning, tightening and/or loosening messages to the wearer of the system 10 via, for example, the user interface 24. Other techniques may also be used to optimize the heart rate measurements.

Figure 4:
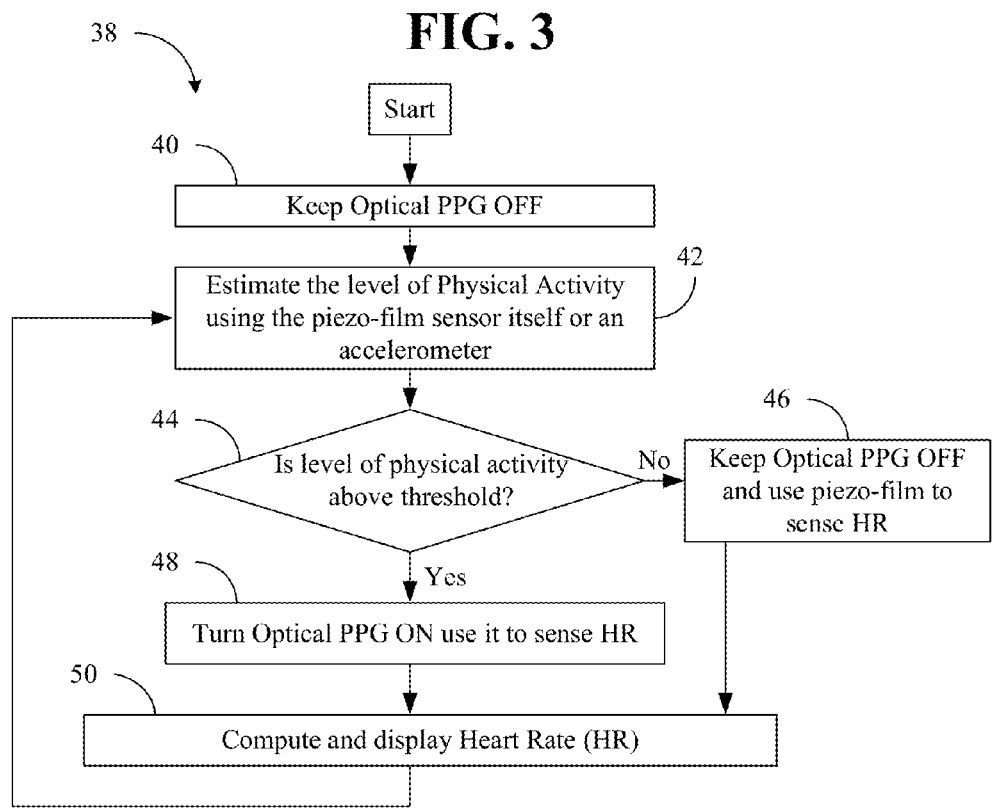
FIG. 4 is a flowchart of an example of a method of generating continuous heart rate measurements according to an embodiment.

Turning now to FIG. 4, a method 38 of generating heart rate measurements is shown. The method 38 may be implemented as one or more modules in a set of logic instructions stored in a machine- or computer-readable storage medium such as random access memory (RAM), read only memory (ROM), programmable ROM (PROM), firmware, flash memory, etc., in configurable logic such as, for example, programmable logic arrays (PLAs), field programmable gate arrays (FPGAs), complex programmable logic devices (CPLDs), in fixed-functionality hardware logic using circuit technology such as, for example, application specific integrated circuit (ASIC), complementary metal oxide semiconductor (CMOS) or transistor-transistor logic (TTL) technology, or any combination thereof.

Illustrated processing block 40 places an optical module in a deactivated state (e.g., kept off), wherein an estimation of the level of physical activity may be made at block 42. The estimation may use signals from a piezoelectric film and/or an accelerometer of a wearable system. Illustrated block 44 determines whether the level of physical activity exceeds a particular threshold (e.g., a physical activity condition is met). If not, the optical module may be maintained in the deactivated state at block 46 and excitation signals from the piezoelectric film may be used to generate heart rate measurements. Block 46 may therefore involve using the piezoelectric film to generate an excitation signal in response to pressure variations on a surface of the piezoelectric film and generating a measurement signal based on the excitation signal, as already discussed. Only if the physical activity condition is met, block 48 may activate the optical module and obtain a measurement signal from the optical module. Illustrated block 50 computes and displays a heart rate measurement based on either the measurement signal from the piezoelectric film or the measurement signal from the optical module. In either instance, the heart rate measurement may be continuous.

ADDITIONAL NOTES AND EXAMPLES

Example 1 may include an apparatus to generate heart rate measurements, comprising a piezoelectric film to generate an excitation signal in response to pressure variations on a surface of the piezoelectric film, an analog front end coupled to the piezoelectric film, the analog front end to generate a first measurement signal based on the excitation signal, a heart rate monitor coupled to the analog front end, the heart rate monitor to generate a continuous heart rate measurement based on the first measurement signal, an optical module coupled to the heart rate monitor, and an activity level monitor coupled to the optical module, the activity level monitor to activate the optical module in response to a physical activity condition being met and deactivate the optical module in response to the physical activity condition not being met, wherein the optical module is to generate a second measurement signal when the optical module is activated, and wherein the heart rate monitor is to generate the continuous heart rate measurement based on the second measurement signal when the second measurement signal is received from the optical module.

Example 2 may include the apparatus of Example 1, wherein the analog front end includes a single stage amplifier.

Example 3 may include the apparatus of Example 1, wherein the activity level monitor is to determine whether the physical activity condition is met based on the first measurement signal.

Example 4 may include the apparatus of Example 1, wherein the activity level monitor is to determine whether the physical activity condition is met based on an accelerometer signal.

Example 5 may include a wearable system comprising a wristband including a piezoelectric film with a surface exposed to an interior region of the wristband, the piezoelectric film to generate an excitation signal in response to pressure variations on the surface of the piezoelectric film, an electrical housing coupled to the wristband, the electrical housing including an analog front end coupled to the piezoelectric film, the analog front end to generate a first measurement signal based on the excitation signal, a heart rate monitor coupled to the analog front end, the heart rate monitor to generate a heart rate measurement based on the first measurement signal, and a user interface coupled to the heart rate monitor, the user interface to output the heart rate measurement.

Example 6 may include the wearable system of Example 5, wherein the analog front end includes a single stage amplifier.

Example 7 may include the wearable system of Example 5, further including an optical module coupled to the heart rate monitor; and an activity level monitor coupled to the optical module, the activity level monitor to activate the optical module in response to a physical activity condition being met, wherein the optical module is to generate a second measurement signal when the optical module is activated, and wherein the heart rate monitor is to generate the heart rate measurement based on the second measurement signal when the second measurement signal is received from the optical module.

Example 8 may include the wearable system of Example 7, wherein the activity level monitor is to deactivate the optical module in response to the physical activity condition not being met.

Example 9 may include the wearable system of Example 7, wherein the activity level monitor is to determine whether the physical activity condition is met based on the first measurement signal.

Example 10 may include the wearable system of Example 7, further including an accelerometer to generate an accelerometer signal, wherein the activity level monitor is to determine whether the physical activity condition is met based on the accelerometer signal.

Example 11 may include the wearable system of any one of Examples 5 to 10, wherein the heart rate measurement is continuous.

Example 12 may include an apparatus to generate heart rate measurements, comprising a piezoelectric film to generate an excitation signal in response to pressure variations on a surface of the piezoelectric film, an analog front end coupled to the piezoelectric film, the analog front end to generate a first measurement signal based on the excitation signal, and a heart rate monitor coupled to the analog front end, the heart rate monitor to generate a heart rate measurement based on the first measurement signal.

Example 13 may include the apparatus of Example 12, wherein the analog front end includes a single stage amplifier.

Example 14 may include the apparatus of Example 12, further including an optical module coupled to the heart rate monitor; and an activity level monitor coupled to the optical module, the activity level monitor to activate the optical module in response to a physical activity condition being met, wherein the optical module is to generate a second measurement signal when the optical module is activated, and wherein the heart rate monitor is to generate the heart rate measurement based on the second measurement signal when the second measurement signal is received from the optical module.

Example 15 may include the apparatus of Example 14, wherein the activity level monitor is to deactivate the optical module in response to the physical activity condition not being met.

Example 16 may include the apparatus of Example 14, wherein the activity level monitor is to determine whether the physical activity condition is met based on the first measurement signal.

Example 17 may include the apparatus of Example 14, wherein the activity level monitor is to determine whether the physical activity condition is met based on an accelerometer signal.

Example 18 may include the apparatus of any one of Examples 12 to 17, wherein the heart rate measurement is continuous.

Example 19 may include a method of generating heart rate measurements, comprising generating an excitation signal in response to pressure variations on a surface of a piezoelectric film, generating a first measurement signal based on the excitation signal, and generating a heart rate measurement based on the first measurement signal.

Example 20 may include the method of Example 19, further including using a single stage amplifier to generate the first measurement signal.

Example 21 may include the method of Example 19, further including activating an optical module in response to a physical activity condition being met, wherein the optical module generates a second measurement signal when the optical module is activated, and wherein the heart rate measurement is generated based on the second measurement signal when the second measurement signal is received from the optical module.

Example 22 may include the method of Example 21, further including deactivating the optical module in response to the physical activity condition not being met.

Example 23 may include the method of Example 21, further including determining whether the physical activity condition is met based on the first measurement signal.

Example 24 may include the method of Example 21, further including determining whether the physical activity condition is met based on an accelerometer signal.

Example 25 may include the method of any one of Examples 19 to 24, wherein the heart rate measurement is continuous.

Example 26 may include an apparatus to generate heart rate measurements, comprising means for performing the method of any of Examples 19 to 25, in any combination or sub-combination thereof.

Thus, techniques may enable continuous heart rate measurements to be made without concern over power consumption, battery life, skin color, muscle tissue perfusion, and so forth. Additionally, fewer parts and less PCB space may be achieved.

Embodiments are applicable for use with all types of semiconductor integrated circuit ("IC") chips. Examples of these IC chips include but are not limited to processors, controllers, chipset components, programmable logic arrays (PLAs), memory chips, network chips, systems on chip (SoCs), SSD/NAND controller ASICs, and the like. In addition, in some of the drawings, signal conductor lines are represented with lines. Some may be different, to indicate more constituent signal paths, have a number label, to indicate a number of constituent signal paths, and/or have arrows at one or more ends, to indicate primary information flow direction. This, however, should not be construed in a limiting manner. Rather, such added detail may be used in connection with one or more exemplary embodiments to facilitate easier understanding of a circuit. Any represented signal lines, whether or not having additional information, may actually comprise one or more signals that may travel in multiple directions and may be implemented with any suitable type of signal scheme, e.g., digital or analog lines implemented with differential pairs, optical fiber lines, and/or single-ended lines.

Example sizes/models/values/ranges may have been given, although embodiments are not limited to the same. As manufacturing techniques (e.g., photolithography) mature over time, it is expected that devices of smaller size could be manufactured. In addition, well known power/ground connections to IC chips and other components may or may not be shown within the figures, for simplicity of illustration and discussion, and so as not to obscure certain aspects of the embodiments. Further, arrangements may be shown in block diagram form in order to avoid obscuring embodiments, and also in view of the fact that specifics with respect to implementation of such block diagram arrangements are highly dependent upon the platform within which the embodiment is to be implemented, i.e., such specifics should be well within purview of one skilled in the art. Where specific details (e.g., circuits) are set forth in order to describe example embodiments, it should be apparent to one skilled in the art that embodiments can be practiced without, or with variation of, these specific details. The description is thus to be regarded as illustrative instead of limiting.

The term "coupled" may be used herein to refer to any type of relationship, direct or indirect, between the components in question, and may apply to electrical, mechanical, fluid, optical, electromagnetic, electromechanical or other connections. In addition, the terms "first", "second", etc. may be used herein only to facilitate discussion, and carry no particular temporal or chronological significance unless otherwise indicated.

As used in this application and in the claims, a list of items joined by the term "one or more of" may mean any combination of the listed terms. For example, the phrases "one or more of A, B or C" may mean A, B, C; A and B; A and C; B and C; or A, B and C.

Those skilled in the art will appreciate from the foregoing description that the broad techniques of the embodiments can be implemented in a variety of forms. Therefore, while the embodiments have been described in connection with particular examples thereof, the true scope of the embodiments should not be so limited since other modifications will become apparent to the skilled practitioner upon a study of the drawings, specification, and following claims.

We claim:

1. An apparatus comprising:
   a piezoelectric film to generate an excitation signal in response to pressure variations on a surface of the piezoelectric film;
   an analog front end coupled to the piezoelectric film, the analog front end to generate a first measurement signal based on the excitation signal;
   a heart rate monitor coupled to the analog front end, the heart rate monitor to generate a continuous heart rate measurement based on the first measurement signal;
   an optical module, implemented at least partly in one or more of configurable logic or fixed functionality logic hardware, coupled to the heart rate monitor; and
   an activity level monitor coupled to the optical module, the activity level monitor to activate the optical module in response to a physical activity condition being met and deactivate the optical module in response to the physical activity condition not being met, wherein the optical module is to generate a second measurement signal when the optical module is activated, and wherein the heart rate monitor is to generate the continuous heart rate measurement based on the second measurement signal when the second measurement signal is received from the optical module.

2. The apparatus of claim 1, wherein the analog front end includes a single stage amplifier.

3. The apparatus of claim 1, wherein the activity level monitor is to determine whether the physical activity condition is met based on the first measurement signal.

4. The apparatus of claim 1, wherein the activity level monitor is to determine whether the physical activity condition is met based on an accelerometer signal.

5. A wearable system comprising:
   a wristband including a piezoelectric film with a surface exposed to an interior region of the wristband, the piezoelectric film to generate an excitation signal in response to pressure variations on the surface of the piezoelectric film; and
   an electrical housing coupled to the wristband, the electrical housing including:
      an analog front end coupled to the piezoelectric film, the analog front end to generate a first measurement signal based on the excitation signal,
      a heart rate monitor coupled to the analog front end, the heart rate monitor to generate a heart rate measurement based on the first measurement signal, and
      a user interface coupled to the heart rate monitor, the user interface to output the heart rate measurement.

6. The wearable system of claim 5, wherein the analog front end includes a single stage amplifier.

7. The wearable system of claim 5, further including:
   an optical module, implemented at least partly in one or more of configurable logic or fixed functionality logic hardware, coupled to the heart rate monitor; and
   an activity level monitor coupled to the optical module, the activity level monitor to activate the optical module in response to a physical activity condition being met, wherein the optical module is to generate a second measurement signal when the optical module is activated, and wherein the heart rate monitor is to generate the heart rate measurement based on the second measurement signal when the second measurement signal is received from the optical module.

8. The wearable system of claim 7, wherein the activity level monitor is to deactivate the optical module in response to the physical activity condition not being met.

9. The wearable system of claim 7, wherein the activity level monitor is to determine whether the physical activity condition is met based on the first measurement signal.

10. The wearable system of claim 7, further including an accelerometer to generate an accelerometer signal, wherein the activity level monitor is to determine whether the physical activity condition is met based on the accelerometer signal.

11. The wearable system of claim 5, wherein the heart rate measurement is continuous.

12. An apparatus comprising:
   a piezoelectric film to generate an excitation signal in response to pressure variations on a surface of the piezoelectric film;
   an analog front end coupled to the piezoelectric film, the analog front end to generate a first measurement signal based on the excitation signal; and
   a heart rate monitor coupled to the analog front end, the heart rate monitor to generate a heart rate measurement based on the first measurement signal.

13. The apparatus of claim 12, wherein the analog front end includes a single stage amplifier.

14. The apparatus of claim 12, further including:
   an optical module, implemented at least partly in one or more of configurable logic or fixed functionality logic hardware, coupled to the heart rate monitor; and
   an activity level monitor coupled to the optical module, the activity level monitor to activate the optical module in response to a physical activity condition being met, wherein the optical module is to generate a second measurement signal when the optical module is activated, and wherein the heart rate monitor is to generate the heart rate measurement based on the second measurement signal when the second measurement signal is received from the optical module.

15. The apparatus of claim 14, wherein the activity level monitor is to deactivate the optical module in response to the physical activity condition not being met.

16. The apparatus of claim 14, wherein the activity level monitor is to determine whether the physical activity condition is met based on the first measurement signal.

17. The apparatus of claim 14, wherein the activity level monitor is to determine whether the physical activity condition is met based on an accelerometer signal.

18. The apparatus of claim 12, wherein the heart rate measurement is continuous.

\* \* \* \* \*